US00PP10408P

United States Patent [19]

van Andel

[11] Patent Number: Plant 10,408

[45] Date of Patent: May 19, 1998

[54] ALSTROEMERIA PLANT VARIETY NAMED 'STAPRINAG'

[75] Inventor: Jacob van Andel, Aalsmeer, Netherlands

[73] Assignee: Van Staaveren b.v., Aalsmeer, Netherlands

[21] Appl. No.: 716,485

[22] Filed: Sep. 16, 1996

[51] Int. Cl.[6] ..... A01H 5/00

[52] U.S. Cl. ..... Plt./87.1

[58] Field of Search ..... Plt./87.1

[56] References Cited

U.S. PATENT DOCUMENTS

| | | | |
|---|---|---|---|
| P.P. 4,930 | 11/1982 | van Andel | Plt./87.1 |
| P.P. 6,661 | 3/1989 | Zelderen | Plt./87.1 |
| P.P. 8,261 | 6/1993 | van Andel | Plt./87.1 |
| P.P. 8,738 | 5/1994 | van Andel | Plt./87.1 |
| P.P. 8,740 | 5/1994 | van Andel | Plt./87.1 |

*Primary Examiner*—James R. Feyrer
*Assistant Examiner*—Kent L. Bell
*Attorney, Agent, or Firm*—Christie, Parker & Hale, LLP

[57] ABSTRACT

A new and distinct Alstroemeria plant variety producing flowers of good quality and attractive coloration, suitable for growing in pots.

1 Drawing Sheet

BACKGROUND OF THE INVENTION

The present invention relates to a new and distinct variety of Alstroemeria hybrid originated as a seedling by crossing as seed parent an unreleased, unpatented seedling identified as 91D213-3 and as pollen parent an unreleased, unpatented seedling identified as 87G1069-02 from among my collection of Alstroemeria seedlings maintained under controlled conditions in a greenhouse at Van Staaveren B.V., Aalsmeer, The Netherlands, for developmental purposes. The varietal denomination of the new variety is 'Staprinag'.

The first act of asexual reproduction of 'Staprinag' was in Aalsmeer, The Netherlands, by propagation by dividing rootstocks. Asexual reproduction in Aalsmeer, The Netherlands, through successive generations has demonstrated that the combination of characteristics as herein disclosed for 'Staprinag' are firmly fixed and retained through successive generations of asexual reproduction.

'Staprinag' has not been observed under all possible environmental conditions. Phenotypic expression may vary with variations in environment such as temperature, light intensity, day length and growing and cultural conditions.

SUMMARY OF THE INVENTION

Flowers of the new variety of Alstroemeria, 'Staprinag' are characterized by flowers of unusual coloration, as described herein. The plant blooms profusely in the Spring and Fall, which is a desirable characteristic in a cut flower variety. 'Staprinag' is especially suitable for growing in pots.

DESCRIPTION OF ILLUSTRATIONS

The new variety of Alstroemeria hybrid is illustrated in the accompanying illustration, which shows typical growth and flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

Botanical classification:
- *Family.*—Amaryllidaceae
- *Genus.*—Alstroemeria sp.
- *Commercial.*—Alstroemeria hybrid.

Origin: Seedling.

Plant

Form: Bush, pot-type.
Shape: Upright.
Height: About 25 to 40 cm.
Main stem or cane length: About 30 cm.
Growth: Vigorous.
Strength: Strong.
Foliage:
- *Quantity.*—Abundant.
- *Number of leaves.*—About 20 to 25.
- *Size of leaf.*—Length: About 3 to 10 cm. Width: About 1 to 2 cm.
- *Shape of leaf.*—Elliptical.
- *Margin type.*—Straight.
- *Texture.*—Smooth.
- *Color.*—Upper side: Near 143A. Underside: Near 143B.
- *Rhizomes.*—Yes. Color: Near 155D. Size: About 10–15 cm.

Inflorescence—Flower/Floret

Blooming habit: Intermittent.
Blooms: Profusely.
- *Spring.*—Yes.
- *Fall.*—Yes.
- *Has tendency to give few blooms in fall.*—No.

Size: Medium.
- *Diameter.*—About 5 to 6 cm.
- *Depth.*—About 4 to 5 cm.

Borne: Singly along simple racemes.
Shape or form:
- *When bloom first opens.*—Cup.
- *When bloom matures.*—Cup.

Petalage:
- *Number of petals.*—6.
- *Arrangement.*—Two concentric circles of 3 petals.
- *Form: Obovate.*

*Margin type.*—Minutely crimped.
*Apex.*—Pointed.
*How long do petals stay on stem?*—About 3 weeks.
*Texture.*—Leathery.
*Appearance.*—Shiny.
*Color.*—Outer petal: Body near 155D to 63D; base near 63D; reverse side near 155D to 63D; 0 to 2 stripes, near 185A. Inside petal: Body near 155D to 2B; base near 63D; reverse side near 155D to near 2B; about 40 to 50 stripes, near 185A.

Peduncle or flower stem;
*Length.*—About 2 to 3 cm.
*Color.*—Near 143A.
*Strength.*—Strong.
*Upright.*—Yes.

Discoloration after full bloom? No.
Is bloom affected by wet or hot weather? No.
Persistence (does flower hang on and dry?): No.
Disease resistance: Unknown.
Fragrance: None.
Lasting quality:
*On plant.*—About 3 weeks.
*As cut flower.*—About 14 days.

Bud

Size:
*Diameter.*—About 1 cm.
*Depth or length.*—About 2 cm.

Form or shape: Pear-shaped.
*Long.*—Yes.
*Pointed.*—No, ovoid.

Rate of opening: Fast.
Color of petals:
*When petals begin to unfurl.*—Near 150D.

Peduncle or flower stem:
*Length.*—About 2 to 3 cm.
*Hairy.*—No.
*Strength or character.*—Erect.
*Color.*—Near 143A.

Reproductive Organs

Stamen:
*Number.*—6.
*Arrangement.*—Around the style.

Anthers:
*Size.*—About 8 to 10 mm.
*Color.*—Near 152C.

Filaments:
*Length.*—About 5 cm.
*Color.*—Near 65C.

Pollen:
*Color.*—Near 152A.

Pistils:
*Number.*—1.

Styles:
*Length.*—About 4 to 5 cm.
*Color.*—Near 65D.

Stigmas:
*Color.*—Near 155D.

Fruit

Fertile: Yes.
Shape: Round.
Color at maturity: Near 164A.

I claim:

1. A new variety of Alstroemeria plant substantially as herein shown and described, suitable for growing in pots.

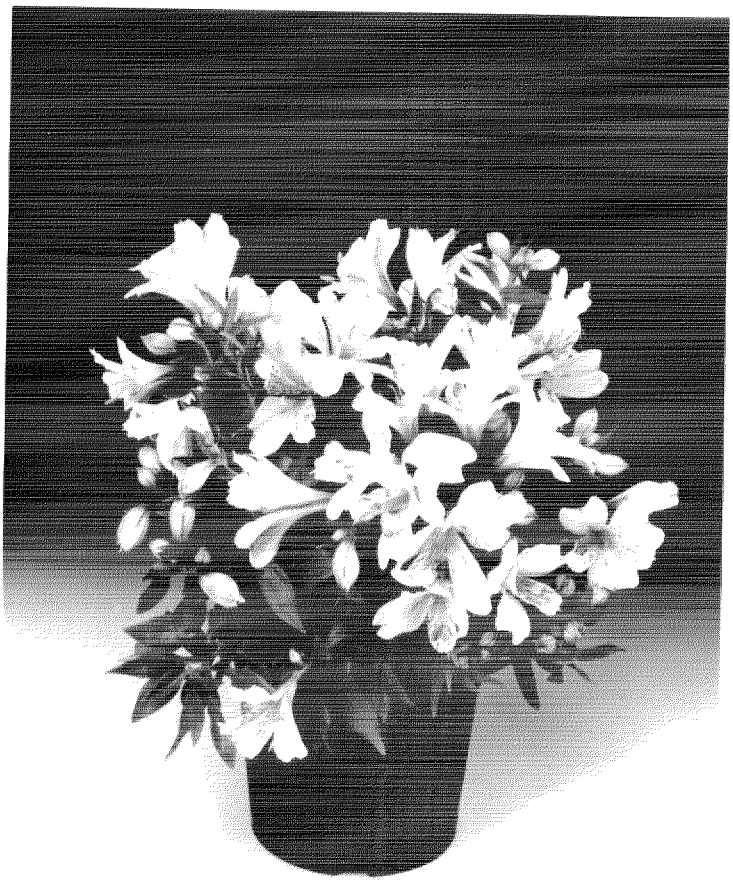

* * * * *